United States Patent [19]

Hwang et al.

[11] Patent Number: 5,106,963

[45] Date of Patent: Apr. 21, 1992

[54] PHOSPHOLIPID CONJUGATES AND THEIR PREPARATION

[75] Inventors: Deng R. Hwang, Tarrytown; Mary E. Scott, Mount Vernon; Eddie Hedaya, Hartsdale, all of N.Y.

[73] Assignee: Miles, Inc., successor in interest to Technicon Instruments Corp., Tarrytown, N.Y.

[21] Appl. No.: 722,658

[22] Filed: Jun. 28, 1991

Related U.S. Application Data

[60] Division of Ser. No. 224,195, Jul. 21, 1988, Pat. No. 5,053,497, which is a continuation of Ser. No. 687,135, Dec. 28, 1984, abandoned.

[51] Int. Cl.⁵ .................. C07H 19/10; C07H 19/20; G01N 31/00; G01N 33/16
[52] U.S. Cl. ..................... 536/27; 536/28; 536/29; 536/5; 536/6.1; 424/11; 424/1.1; 424/45; 514/178; 514/958; 435/7.9; 436/523
[58] Field of Search .............. 536/6.1, 5, 27, 28, 536/29; 514/958; 424/1.1, 12, 45; 436/829

[56] References Cited

U.S. PATENT DOCUMENTS

| 4,193,983 | 3/1980 | Ullmann et al. | 436/829 |
| 4,323,560 | 4/1982 | Baschang et al. | 536/53 |
| 4,515,736 | 5/1985 | Deamer | 436/829 |
| 4,797,479 | 1/1989 | Shuto et al. | 536/27 |
| 4,921,951 | 5/1990 | Shuto et al. | 536/27 |

FOREIGN PATENT DOCUMENTS

5309235 12/1985 European Pat. Off. .

*Primary Examiner*—Ronald W. Griffin
*Assistant Examiner*—Louise Leary
*Attorney, Agent, or Firm*—Morgan & Finnegan

[57] ABSTRACT

Phospholipid conjugate compounds derived from cardiac glycosides and steroids useful in liposome immunoassays are disclosed as well as their method of preparation.

9 Claims, No Drawings

PHOSPHOLIPID CONJUGATES AND THEIR PREPARATION

CROSS REFERENCE TO RELATED APPLICATIONS

This application is a divisional of application Ser. No. 07/224,195, filed Jul. 21, 1988, now U.S. Pat. No. 5,053,497, which is a continuation of application Ser. No. 06/687,135, filed Dec. 28, 1984, now abandoned.

BACKGROUND OF THE INVENTION

This invention relates to novel immunoreactive phospholipid conjugates useful for homogeneous liposome immunoassays. More particularly, this invention provides a rapid and efficient approach to digoxin and digoxin-related phospholipid conjugates which are useful for liposome immunoassay. In one novel aspect, a synthetic procedure is provided which involves the linking of a terminal sugar group, e.g., digitoxose of digoxin, to a phospholipid through a carboxymethyl oxime functionality. Such procedure provides much improved yields of readily purified products compared to known procedures. Moreover, it is applicable to related phospholipid conjugates where linkage through a sugar ring is highly preferred, i.e. digitoxin, gitoxin, ouabain, digitonin and other related cardiac glycosides. In addition to these cardiac glycosides, other glycosides including those from the saponin class, but not limited to that class, are within the purview of this invention.

Still further, the method of this invention is also applicable to phospholipid conjugates derived from steroids such as estrogens and testosterones which can be modified to form oxime derivatives remote from key functionalities important for immunorecognition by specific antibodies. The novel phospholipid conjugates disclosed herein are useful for sensitive liposome immunoassays, e.g., for digoxin.

Digoxin is a potent cardiac glycoside. Toxic amounts of digoxin exert undesirable and potentially lethal electrophysiological effects [Hoffman et al, The Pharmacological Basis of Therapeutics, Gilman, 6th ed., p 729, N.Y. 1980]. Accordingly, various immunoassay methods for cardiac glycosides are now widely used clinically as aids in the determination of appropriate dosage schedules for patients receiving these drugs. Because digoxin is too small a molecule to be antigenic by itself, it is necessary to conjugate digoxin convalently as a hapten to antigenic carriers, for example, human serum albumin (HSA), bovine serum albumin (BSA) or keyhole limpet hemocyanin (KLH) in order to elicit digoxin-specific antibodies in experimental animals for use in immunoassay. The preparation of immunoreactive digoxin derivatives is typically carried out by the procedure of Butler et al [Proc. Natl. Acad. Sci., U.S.A., 1967, 57, 71–78; and Methods in Enzymology, Academic Press, 84, 558–577 (1982)] which is based on the work of Erlanger and Beiser, Proc. Natl. Acad. Sci., 52, 68 (1964). The reaction sequence involved periodate cleavage of the terminal sugar ring (digitoxose or rhamnose) followed by reaction with a protein carrier, enzyme or related biological molecule, and finally reductive amination with sodium borohydride. Thus, digoxin-HSA (Butler et al supra), digoxin-BSA [Smith et al, Biochemistry, 9, 331–337 (1970)], mellitin-Ouabain [Freytag et al, J. of Immunological Methods, 70, 133–140 (1984)], and digoxin-dibenzo-18-crown-6 [Keating et al, Anal. Chem. 56, 801–806 (1984)] conjugates have been prepared using the aforementioned reaction sequence.

U.S. Pat. No. 4,115,539 discloses a method of preparing digoxin conjugates using isocyanates based upon tyrosine methyl ester. U.S. Pat. Nos. 4,297,273 and 4,363,759 disclose ways to prepare chemiluminescent phthalaldehyde-labeled digoxigenin. U.S. Pat. No. 4,342,826 employs the procedure of Butler et al supra to prepare a non-characterized digoxin-phosphatidylethanolamine conjugate but, this preparation in our hands, resulted in a very complex mixture.

Hence, the present invention satisfies a strong need for digoxin and digoxin-related phospholipid conjugates and other conjugates useful for sensitive liposome immunoassays.

The novel synthesis, disclosed herein, involves the linking of a dialdehyde intermediate, e.g. digoxin dialdehyde, through a carboxymethyl oxime functionality resulting in significantly high yields of readily purified products.

SUMMARY OF THE INVENTION

In accordance with this invention, there is disclosed and claimed a phospholipid conjugate compound of the formulae:

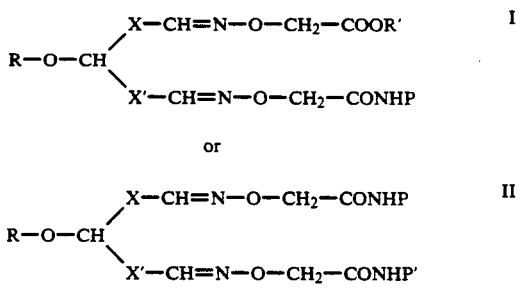

or

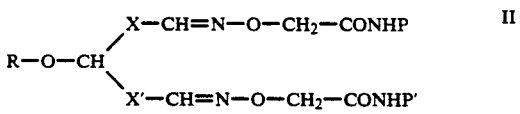

wherein R is derived from an organic compound containing 1,2-dihydroxy groups which groups are subject to oxidative cleavage; X and X' are the side chain moieties connecting the carbon atoms resulting from oxidative cleavage of the 1,2-dihydroxy groups which the R moiety; and P and P' are phospholipid ethanolamine moieties.

In one embodiment, R is derived from a cardiac glycoside such as digoxin, digitoxin, gitoxin, ouabain, digitonin and the like. For compounds of Formula I, R' is preferably H and P is a phospholipid moiety, preferably, the phospholipid derived from dipalmitoyl phosphatidyl ethanolamine. For compounds of Formula II, P and P' are phospholipid moieties, preferably derived from dipalmitoyl phosphatidyl ethanolamine. Other suitable phospholipid moieties may be desired to introduce modified properties of the liposome. These include the natural phosphatidyl ethanolamines, dimyristyl phosphatidyl ethanolamine, phosphatidyl serine, etc.

In another embodiment of this invention, compounds are included having the formula

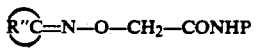

wherein R" is derived from a steroid having at least one carbonyl group, said carbonyl group forming said oximino moiety =N—O—, and P is a phospholipid ethanolamine moiety.

Preferably, P is derived from dipalmitoyl phosphatidyl ethanolamine (DPPE), Illustrative steroids include testosterone and 6-keto-estradiol.

In another embodiment, the steroid contains one or more carbonyl groups, at least one of which forms the oximino moiety to which said phospholipid moiety is attached.

In another embodiment, the steroid contains 1,2-dihydroxy groups, which groups are subject to oxidative cleavage, and the oximino moieties are connected to the carbon atoms resulting from oxidative cleavage and to the ethanolamine phospholipid moieties.

In general, the novel phospholipid conjugates of this invention are derived from compounds having functional groups which can be modified and/or converted to form oxime derivatives.

The novel method of preparing compounds having formulae shown above are also within the purview of this invention.

A liposomal immunoassay such as that disclosed in U.S. Pat. No. 4,342,826 or U.S. Pat. No. 4,235,792, incorporated by reference herein, which uses the herein disclosed compounds, is also within the scope of this invention.

DETAILED DESCRIPTION OF THE INVENTION

The synthetic sequence for preparing the novel phospholipid conjugates of this invention is shown, using digoxin as a preferred illustration, in Scheme A provided hereinafter.

periodate under nitrogen atmosphere. Thin layer chromatography (silica gel, Merck) with the solvent system chloroform/methanol (10/1 by volume)shows one homogeneous spot at $R_f$0.16 (detected by spraying with methanol/concentrated sulfuric acid(9/1 by volume, and warming briefly to develop a dark brown color. The condensation reaction of digoxin dialdehyde and carboxy methoxyamine hemihydrochloride proceeds rapidly in sodium acetate/ethanol under nitrogen atmosphere. Quantitative yields of di-(O-carboxymethyl) oxime (TLC: $R_f$0.04–0.12 solvent system chloroform/methanol 6/1 by volume) were obtained. The digoxin dioxime derivative was used immediately in the next reaction step. The carboxy functionalities of the dioxime are then reacted with N-hydroxysuccinimide in the presence of dicyclohexylcarbodiimide to give an active ester. The dioxime active ester is then condensed with dipalmitoyl phosphatidylethanolamine (DPPE) with gentle heating for seventy-two hours. The reaction was monitored closely by TLC. Thin layer chromatography with the solvent system chloroform/methanol/water(75/25/3 by volume, showed two major components at $R_f$0.20 and 0.13 along with N-hydroxysuccinimide at $R_f$0.30. The phospholipid moiety of the conjugates was detected by molybdate blue spray. The excess N-hydroxysuccinimide was removed from the reaction mixture by preparative LC (Kieselgel, 200 g, glass column (2.5×50 cm), solvent system chloroform/methanol/water(2/8/1 by volume)). Pure digoxin-di-DPPE conjugate (0.1348 g, 20%; $R_f$0.30) and digoxin-mono DPPE conjugate (0.1424 g, 26.5%; $R_f$0.15) were isolated from crude reaction mixture by preparative Scheme A
Synthesis Of Digoxin-DPPE Conjugates

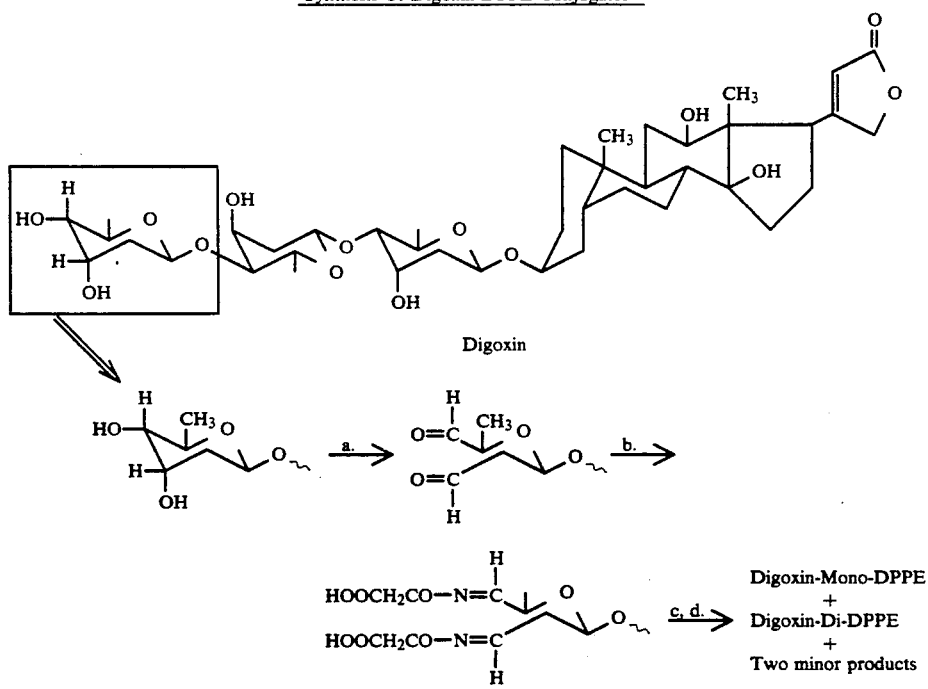

a. sodium periodate
b. (NH₂OCH₂COOH)₂·HCl/NaOAc + EtOH
c. NHS + D.C.C. ——→ active ester
d. dipalmitoyl phosphatidyl ethanolamine/CHCl₃/Et₃N
   (DPPE)

The terminal digitoxose in digoxin is cleaved to give dialdehyde in quantitative yield by using, e.g., sodium TLC in chloroform/methanol/water (2/8/1 by volume). Two other minor products were also isolated. The structures of the minor products were not identified.

The structure proof of the two major conjugates was extracted from the IR, UV, high resolution proton NMR spectra, and fast atom bombardment (FAB) mass spectra.

The advantages of the abovedescribed synthetic procedure resides in its ability and facility to efficiently provide a relatively stable, storable, yet activatable, oxime intermediate. This intermediate overcomes the disadvantages inherent in the Butler et al procedure discussed earlier. These include the propensity for the dialdehyde intermediate to undergo deleterious side-reactions, particularly in the presence of amine derivatives of lesser reactivities such as phospholipids. An additional advantage is that the claimed procedure provides products which can be readily isolated, characterized and purified in contrast to Butler, which to our knowledge, yields a sufficiently complex mixture thwarting the desired product characterization.

The synthetic method described herein is also applicable to the preparation of analogous phospholipid conjugates involving linkage through a sugar ring such as digitoxin, gitoxin, ouabain, digitonin and related cardiac glycosides, or those involving steroids which can be modified, to form oxime derivatives remote from key functionalities important for immunorecognition by specific antibodies.

EXAMPLE I

Synthesis of Digoxin DPPE Conjugates

A) Digoxin Dialdehyde

Digoxin (0.4985 g, 0.64 mmole) was dissolved in 10 ml of chloroform/methanol (3/1.5) and placed into a 100 ml two-necked flask. Sodium periodate (0.3102 g, 1.4 mmoles) was dissolved in 4 ml distilled water and placed into a pressure equalized addition funnel. The periodate solution was slowly added to the flask while stirring and under nitrogen. A white precipitate was immediately formed and the reaction was complete within 15 minutes after addition of the periodate. Reaction progress was monitored by TLC (E. M. Merck, pre-coated TLC sheets, silica gel 60 F254 0.2 mm thickness) in chloroform/methanol 10/1 by volume $R_f$ 0.16=dialdehyde, one homogeneous spot; $R_f$ 0.07=Digoxin. Both spots became dark brownish when the TLC plate was sprayed with methanol/concentrated sulfuric acid (9/1 by volume) and placed in an oven at 100° C. The reaction mixture was evaporated on a rotatory evaporator and brought up in 30 ml of chloroform and 3 ml of water. The cloudy solution was extracted and the aqueous layer washed three times with 10 ml chloroform. The organic phases are combined (60 ml) and dried over magnesium sulfate. The organic solvents are evaporated to dryness. A light yellow brownish oily material was left. This material was used immediately in the next reaction.

B) Digoxin Di- (0-carboxymethyl) Oxime

Carboxy methoxylamine hemihydrochloride (0.3119 g, 1.4 mmoles) and sodium acetate (0.2260 g, 1.6 mmoles) were dissolved in 3 ml water and placed into a 50 ml 2-necked flask. The digoxin dialdehyde, dissolved in 1.3 ml ethanol, was placed into a pressure equalized funnel and slowly added to the flask while stirring and under nitrogen. The reaction was complete within ten minutes (TLC: chloroform/methanol 6/1 by volume, $R_f$ 0.09–0.13). The reaction mixture was evaporated to dryness and dissolved in 20 ml ethyl acetate and 3 ml water. The organic layer is separated and the aqueous layer was washed three times with 5.0 ml ethyl acetate. The organic layers were combined and dried over anhydrous magnesium sulfate. The solution was filtered and evaporated to dryness. The residue was dried for 30 minutes under high vacuum (0.1 mm Hg) and used immediately for the next step.

C) Preparation of N-Hydroxysuccinimide Ester of Digoxin Di (O-Carboxymethyl) Oxime Dicyclohexylcarbodiimide (DCC 0.2805 g, 1.3 mmoles) was dissolved in 6 ml dry DMF and placed into a 50 ml 2-necked flask. The solution was cooled in an ice-water bath (4° C.) Digoxin di(O-carboxymethyl) oxime, dissolved in 80 ml DMF, was slowly added while stirring and under nitrogen to the flask. Immediately afterwards, N-hydroxysuccinimide solution (0.1500 g, 1.3 mmoles, in 6 ml DMF) was likewise added. Reaction progress was monitored by TLC [chloroform/methanol/water 75/25/3 by volume, $R_f$ 1.0 (DCC), 0.75 (dioxime NHS active ester), 0.34 (NHS), 0.1 (dioxime). The reaction was continued at 4° C. under nitrogen for 18 hours.

The desired product possessed the following characteristics in TLC: (1) homogeneous UV detectable spot (short wavelength), (2) the homogeneous spot turned brownish when spraying the TLC plate with methanol/concentrated sulfuric acid (9/1 by volume) and warming the plate briefly in 100° C. oven.

The reaction mixture was filtered to remove dicyclohexyl urea and the crude reaction mixture was used for the next step.

D) Preparation of Digoxin-DPPE Conjugates

The crude dioxime active ester (17 ml reaction mixture) was placed into a 100 ml 2-necked flask. A suspension of DPPE (0.4431 g, 0.64 mmoles, dispersed in 30 g ml dry chloroform and 0.7 ml of triethyl amine) was placed into an addition funnel and slowly added to the flask while stirring under nitrogen and being protected from light. The mixture was heated gently (40°–50° C.) and continued for 72 hours. The reaction was monitored by TLC (solvent system chloroform/methanol/water 75/25/3 by volume; $R_f$ 0.75 (active ester), 0.52 (unknown 1), 0.45 (unknown 2), 0.30 (NHS), 0.21 DPPE, 0.20 (disubstituted conjugate), 0.13 (monosubstituted conjugate). The reaction mixture was complex and the above were the major identified products. The phospholipid moiety of the conjugates was detected by molybdate blue spray. The reaction mixture was evaporated and brought up in 10 ml chloroform/methanol/water (2/8/1). The N-hydroxysuccinimide was removed from the mixture by LPLC [(Kiesel gel 200 g, glass column (2.5 cm×50 cm), solvent system chloroform/methanol/water (2/8/1 by volume)]. Pure mono and disubstituted conjugates could be obtained by preparative TLC in chloroform/methanol/water (2/8/1 by volume, $R_f$ 0.30 (disubstituted); 0.15 (monosubstituted). Pure digoxin-di-DPPE conjugate (0.1349 g 20%) and digoxin-mono-DPPE conjugate (0.1424 g 26.5%) were obtained. Two other minor products were also isolated. The structure of the minor products was not identified.

E) NMR, UV, IR and FAB Data

The NMR, UV and IR and fast atom barbardment (FAB) mass spectra data are summarized in Chart 1 and 2 provided hereinbelow:

CHART 1

Digoxin-Mono-DPPE

NMR (300 MHz, CDCl$_3$)
δ  0.8 (singlet, 3H, 18CH$_3$), 0.96 (singlet, 3H, 19 CH$_3$),
   0.90 (triplet, 6H, terminal methyl group in phospholipid)
   2.23–1.05 [(complex multiplet, 83H, 2 (CH$_2$)$_{12}$, 3 CH$_3$ (digitoxose ring), 3 CH$_2$ (digitoxose ring), 8 CH$_2$ (digoxigenin ring), 2 CH$_2$(CH$_2$)$_{12}$]
   2.32 (two overlapping triplets, 4H, 2 CH$_2$CO)
   4.72–3.05 [(complex multiplet, 27H, CH$_2$OCOR, 9 CH (digitoxose ring proton), 6 CH (digoxigenin ring proton), glycero CH$_2$—O—P protons, ethanolamine CH$_2$—O—P, —OCH$_2$—CO— and —CH$_2$—NH)]
   4.95 (multiplet, 5H, CH$_2$ in lactone and 3 protons at C$_1$, C$_{1'}$, and C$_{1''}$ in digitoxose)
   5.25 (multiplet, 1H, —CH—OCOR)
   5.95 (singlet, 1H, lactone, —C=CH)
UV (Cary 219, CHCl$_3$) max. 241 nm (ε 1744)
IR (KBr, Perkin Elmer 1430 ratio reading, cm$^{-1}$): 3435 (broad OH), 2923, 2852, 1743 (ester), 1668, 1622.

CHART 2

Digoxin-Di-DPPE

NMR (300 MHz, CDCl$_3$)
δ  0.82 (singlet, 3H, 18CH$_3$), 0.94 (singlet, 3H, 19 CH$_3$),
   0.90 (triplet, 12H, terminal methyl group in phospholipid)
   2.32 (multiplet, 8H, 4 CH$_2$—CO)
   2.2–1.05 (complex multiplet)
   4.75–2.8 (complex multiplet)
   4.9 (multiplet, 5H, CH$_2$ in lactone and 3 protons at C$_1$, C$_{1'}$, and C$_{1''}$ in digitoxose)
   5.25 (multiplet, 2H, 2 CH—OCOR)
   5.95 (singlet, 1H, Lactone —C=CH)
UV (Cary 219, CHCl$_3$) max. 241 nm (ε 2071)
IR (KBr, Perkin Elmer 1430 ratio reading, cm$^{-1}$): 3427 (broad OH) 2923, 2853, 1781, 1743, 1668.

As a further confirmation of the structure, positive ion fast atom bombardment (FAB) mass spectra ($^m$/Z) from purified conjugates in a thioglycerol matrix were obtained using the MS-50 high resolution mass spectrometer. The most intense peak appeared in the molecular ion region, representing $^m$/Z of (M+metal)$^+$ and the isotopically enriched species. The molecular ion for digoxin-mono-DPPE was 1621 (M+Na)$^+$ and the molecular ion for digoxin-di-DPPE was 2311 (M+K)$^+$.

F) Liposomal Immunoassay

Both conjugates are used in the liposomal immunoassay methods described in U.S. Pat. No. 4,342,826 (e.g. Example X) and in U.S. Pat. No. 4,235,792 with acceptable results.

EXAMPLE II

The procedure of Example I is repeated wherein, in lieu of digoxin, approximate stoichiometric equivalent amounts of the following compounds are used with comparable results:
digitoxin
gitoxin
ouabain
digitonin

EXAMPLE III

The procedure of Example I is repeated wherein, in lieu of dipalmitoyl phosphatidyl ethanolamine, an approximate stoichiometric equivalent amount of dimyristyl phosphatidyl ethanolamine is used to yield the corresponding product.

EXAMPLE IV

The procedure of Example I [(steps B), C) and D)] is repeated except that testosterone is used, in an approximate stoichiometric amount, in lieu of digoxin dialdehyde to obtain the corresponding conjugated phospholipid product.

It should be understood by those skilled in the art that various modifications may be made in the present invention without departing from the spirit and scope thereof as described in the specification and defined in the appended claims.

What is claimed is:

1. A phospholipid conjugate compound having the formula $$R''C=N-O-CH_2-CONHP\ [COOP]$$

wherein R'' is derived from a steroid having at least one carbonyl group, said carbonyl group forming said oximino moiety, =N—O—, and wherein P is a phospholipid ethanolamine moiety.

2. The compound of claim 1 wherein P is derived from dipalmitoyl phosphatidyl ethanolamine (DPPE).

3. The compound of claim 2, wherein said steroid is testosterone or estrogen.

4. The compound of claim 2 wherein said steroid is 6-keto-estradiol.

5. The compound of claim 1 wherein said steroid contains two or more carbonyl groups, at least one of which forms said oximino moiety to which said phospholipid ethanolamine moiety is attached.

6. The compound of claim 1 wherein said steroid contains 1,2-dihydroxy groups, which groups are subject to oxidative cleavage, and said oximino moieties are connected to the carbon atoms resulting from oxidative cleavage and to said ethanolamine phospholipid moieties.

7. A liposomal immunoassay for the determination of appropriate dosage schedules of steroids for human administration which employs the phospholipid conjugate compound as recited in claim 1.

8. A method of preparing the compound of claim 6, comprising the steps of:
   (a) oxidatively cleaving the 1,2-dihydroxy group;
   (b) reacting the dialdehyde group resulting from step (a) with carboxy methoxylamine to form a corresponding dioxime intermediate;
   (c) reacting the dioxime intermediate of step (b) with N-hydroxysuccinimide in the presence of dicyclohexycarbodiimide to form a dioxime active ester; and
   (d) condensing the dioxime active ester with a phospholipid ethanolamine to form the phospholipid conjugate compound.

9. The method of claim 8, wherein formation of reaction products of steps (a) through (d) is monitored by thin layer chromatography.

* * * * *

UNITED STATES PATENT AND TRADEMARK OFFICE
CERTIFICATE OF CORRECTION

PATENT NO. : 5,106,963
DATED : April 21, 1992
INVENTOR(S) : Deng R. Hwang, et al.

It is certified that error appears in the above-identified patent and that said Letters Patent is hereby corrected as shown below:

In Claim 1, Column 8, line 24, remove "[COOP]".

Signed and Sealed this

Eighteenth Day of October, 1994

*Attest:*

BRUCE LEHMAN

*Attesting Officer*   *Commissioner of Patents and Trademarks*